United States Patent
Noel

(10) Patent No.: US 7,629,883 B2
(45) Date of Patent: Dec. 8, 2009

(54) BABY MONITOR HAVING A TEMPORARY MUTE FUNCTION AND METHOD OF USE

(75) Inventor: Peter David Noel, Denver, CO (US)

(73) Assignee: Peter D. Noel, Denver, CO (US)

( * ) Notice: Subject to any disclaimer, the term of this patent is extended or adjusted under 35 U.S.C. 154(b) by 414 days.

(21) Appl. No.: 11/531,275

(22) Filed: Sep. 12, 2006

(65) Prior Publication Data

US 2008/0068155 A1  Mar. 20, 2008

(51) Int. Cl.
*G08B 1/08* (2006.01)

(52) U.S. Cl. .............................. 340/539.15; 340/539.1; 340/539.14; 340/309.16

(58) Field of Classification Search ............ 340/539.15, 340/539.14, 539.1, 531, 530, 3.7, 3.71, 5.3–5.33, 340/825.36–825.52, 870.09; 116/67, 200; 381/94.5, 94.8
See application file for complete search history.

(56) References Cited

U.S. PATENT DOCUMENTS

| | | | | |
|---|---|---|---|---|
| 5,210,532 | A * | 5/1993 | Knoedler et al. | 340/825.69 |
| 6,111,522 | A * | 8/2000 | Hiltz et al. | 340/932.2 |
| 6,150,941 | A | 11/2000 | Geiger et al. | |
| 6,462,664 | B1 | 10/2002 | Cuijpers et al. | |
| 6,593,851 | B1 * | 7/2003 | Bornstein | 340/539.15 |
| 6,759,961 | B2 | 7/2004 | Fitzgerald et al. | |
| 6,792,323 | B2 | 9/2004 | Krzyzanowski et al. | |
| 2003/0122676 | A1 * | 7/2003 | Cuijpers et al. | 340/573.1 |
| 2003/0231778 | A1 * | 12/2003 | Landa | 381/77 |
| 2004/0130449 | A1 | 7/2004 | Hung | |
| 2004/0246136 | A1 | 12/2004 | Sanoner et al. | |
| 2005/0035864 | A1 | 2/2005 | Fitzgerald et al. | |
| 2005/0088298 | A1 * | 4/2005 | Liu | 340/539.15 |
| 2005/0181878 | A1 * | 8/2005 | Danieli et al. | 463/42 |
| 2005/0231356 | A1 | 10/2005 | Bish et al. | |
| 2005/0237164 | A1 | 10/2005 | Finkelstein et al. | |
| 2005/0266813 | A1 * | 12/2005 | Ricard et al. | 455/179.1 |
| 2006/0033809 | A1 * | 2/2006 | Farley | 348/14.01 |
| 2006/0132595 | A1 * | 6/2006 | Kenoyer et al. | 348/14.08 |
| 2007/0222580 | A1 * | 9/2007 | Chapman et al. | 340/539.1 |

OTHER PUBLICATIONS

Philips DECT Deluxe Baby Monitor SCD489, Babyworld, http://shop.babyworld.co.uk/.

* cited by examiner

*Primary Examiner*—Daniel Wu
*Assistant Examiner*—Ryan W Sherwin
(74) *Attorney, Agent, or Firm*—Dorsey & Whitney LLP

(57) ABSTRACT

A system and method for monitoring a baby is disclosed incorporating a parent unit in communication with a baby unit. The parent unit includes a function operable to temporarily mute the substantial reproduction of baby sounds at the parent unit. The parent unit may additionally include a plurality of outputs including a digital display of the time remaining before the temporary mute function is disabled, a visual indication that the substantial reproduction of sound is muted, a visual display indicative of the volume of the baby sounds, and music played when the substantial reproduction of sound is muted. Embodiments of the present invention also include a safety features operable to disable the temporary mute function in possible emergency situations.

20 Claims, 4 Drawing Sheets

BABY MONITOR HAVING A TEMPORARY MUTE FUNCTION AND METHOD OF USE

FIELD OF THE INVENTION

Devices used to remotely monitor a sleeping baby.

BACKGROUND OF THE INVENTION

Parents are faced with the problem of teaching their baby to sleep through the night. This can be particularly problematic when the baby sleeps in a separate room from the parents. Separation from the parents is a new experience for the baby and can be traumatic. As a result, the baby may be unable to sleep or may sleep sporadically, waking-up and crying several times throughout the night. Typically, a parent will come to comfort the baby until the baby falls back asleep. Then the parent will return to his or her bedroom and return to sleep, sometimes being woken-up again a short time later by the baby.

Child development experts, such as Dr. Richard Ferber, advocate an approach to child rearing that attempts to let the baby "cry itself to sleep." In particular, when the baby wakes-up and begins to cry, the parents do not immediately respond by coming to comfort the baby. It is thought that by allowing the baby to cry for a certain amount of time, the baby will gradually learn to master the anxiety of being alone. Initially, the baby may be left alone for a short time. As the baby begins to gain a greater level of comfort with being alone, progressively longer time intervals may become appropriate. This approach to child rearing has become known as the Ferber Method.

Parents seeking to use the Ferber Method may employ the use of a baby monitor. Monitors such as these include a unit maintained in the room with the baby and a unit kept with the parents. The baby unit allows crying or other sounds made by the baby to be picked-up and transmitted to the parent unit. The parent unit receives the transmission from the baby unit allowing the baby sounds to be substantially reproduced in proximity to the parents. Remote monitoring allows a parent and child to sleep in separate rooms. When used in connection with the Ferber Method, the parent unit is turned off or otherwise disabled for a certain amount of time during which the baby is allowed to cry without receiving attention.

Attempting to implement the Ferber Method using prior art baby monitors inevitably leads to problems. In particular, the parents may fall back asleep when the parent unit is disabled. With the parents sleeping and no longer in contact with the baby, the baby may be left to cry for a much longer time than is desirable. A solution to this problem is to disable the baby monitor and to set an alarm clock. If the parents then fall back asleep, they can be assured that they will be woken-up at a predetermined time and the baby will not be left alone for too long. However, this method suffers from the drawback that if the baby does in fact "cry itself to sleep" the parents are still woken-up when the alarm goes off. The parents then lose valuable sleep by having to disable the alarm, possibly having to reset the alarm to a normal waking time, and then having to fall back asleep.

Accordingly, it would be desirable to have a baby monitor with a parent unit that is capable of being muted for a predetermined time after which the parent unit functions normally. Additionally, it would be desirable for the predetermined time in which the baby monitor is muted to be adjustable.

SUMMARY OF THE INVENTION

The present invention is directed to an improved baby monitor and a method for using the improved baby monitor. The present invention includes a baby monitor with a parent unit that features a temporary mute function. When this function is enabled, the parent unit's audio is disabled. In particular, sounds received at the baby unit are not reproduced at the parent unit. After a predetermined time, the temporary mute function is disabled, allowing sounds received at the baby unit to be again substantially reproduced at the parent unit. The parents may adjust the time in which the parent unit remains muted.

In accordance with embodiments of the present invention, the parent unit features an actuator, such as a button disposed on the top of the device, that enables the temporary mute function. An initial actuation of the actuator causes the parent unit to be temporarily muted for an initial amount of time. Subsequent actuations of the actuator thereafter cause additional time intervals to be added to the total amount of time that the parent unit will remain muted. Alternatively, separate actuators may control the mute function enablement and the addition of time intervals.

In accordance with embodiments of the present invention, the parent unit features a display of the time remaining until the temporary mute function will be disabled and the parent unit will again substantially reproduce sounds picked-up by the baby unit. When the parent unit is muted this display provides an indication of the time in which the baby will be allowed to cry.

In accordance with embodiments of the present invention, the parent unit features a visual display indicative of sounds being made by the baby. This feature provides the parents an indication of whether or not the baby is crying at times when the parent unit is muted. This display may be comprised of a plurality of light emitting diodes arranged in a known manner to indicate sound level. Alternatively, liquid crystal displays (LCD) or other known display methods may be used to indicate sound level.

In accordance with embodiments of the present invention, the parent unit features an indicator that signals that the temporary mute function is enabled. This indicator may be a light emitting diode disposed on the face of the device that is illuminated when the temporary muted function is enabled.

In accordance with embodiments of the present invention, the parent unit plays classical music or other musical genres when the temporary mute function is enabled. The parent unit may contain a toggle switch that enables this mode of operation.

In accordance with embodiments of the present invention, the baby monitor includes safety features responsive to sounds made by the baby that cause the temporary mute function to be prematurely disabled. An example of a safety feature within the scope of the invention is a volume threshold. In particular, if the volume of the baby's crying exceeds a certain level this may indicate an emergency situation in need of immediate attention by the parents. Accordingly, at such a sound level the temporary mute function will be disabled and the parent unit will again substantially reproduce sounds made by the baby. Alternative safety features are also within the scope of the invention. In particular, pattern recognition techniques may be used to identify baby cries that are indicative of particular needs.

In accordance with embodiments of the present invention, the improved baby monitor is used by parents to allow their baby to cry for a certain predetermined time. Accordingly, the baby and the baby unit are placed in one room and the parents and the parent unit are located in another room. When the baby awakens during the night and begins to cry, the parents are woken-up by the parent unit that operates to substantially reproduce the baby's cries that have been picked-up by the baby unit. The parents then enable the temporary mute function for a predetermined amount of time and then perhaps fall back asleep. After the predetermined time the temporary mute function is disabled and the parent unit again may substantially reproduce sounds made by the baby. If at this time the baby is still crying, then the parents are again woken-up and may proceed to comfort the baby. Alternatively, if the baby has ceased crying and gone back to sleep, the parents are not woken-up by any sounds and thus continue to sleep.

DETAILED DESCRIPTION

The present invention is directed to a baby monitor system that can be muted when parents wish to allow their baby to cry for a certain time without receiving attention. After a certain time the baby monitor's mute will be disabled and the parents will again hear cries or other sounds made by the baby. Parents may use such a baby monitor in attempt to teach the baby greater independence by allowing it to "cry itself to sleep."

Figure 1:
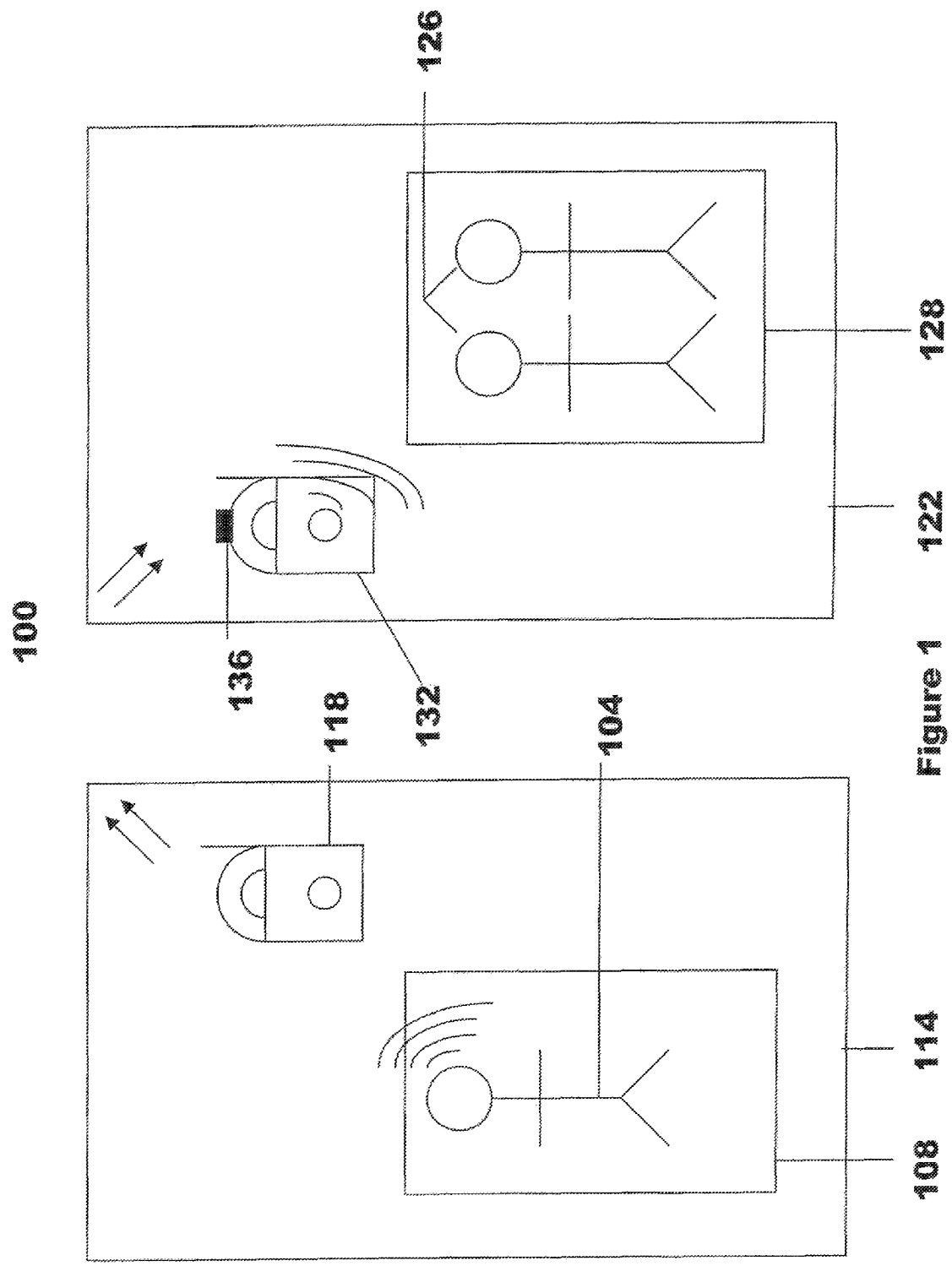
FIG. 1 is a schematic illustration of a baby monitor system in accordance with embodiments of the present invention.

Turning now to FIG. 1, wherein a baby monitoring system 100 in accordance with embodiments of the present invention is illustrated. FIG. 1 shows a baby 104 placed in a crib 108 located in a nursery 114. Nearby is a baby unit 118. The baby unit 118 is placed sufficiently close to the baby's crib 108 to allow crying or other noises made by the baby 104 to be picked up. Additionally, FIG. 1 shows a bedroom 122 where the baby's parents 126 are lying in bed 128. Nearby is a parent unit 132. Parent unit 132 includes an actuator 136 for use in connection with a temporary mute function, as described in greater detail below. As can be appreciated, the parent unit 132 need not be used exclusively in a bedroom. For example, the parent unit 132 may be used in a kitchen at a time when the parents 126 are preparing a meal or in any room at a time when the parents desire to remotely monitor the baby 104. Additionally, the parent unit 132 may be used by other caregivers, such as baby-sitters, that may be in charge of the baby's 104 welfare.

Figure 2:
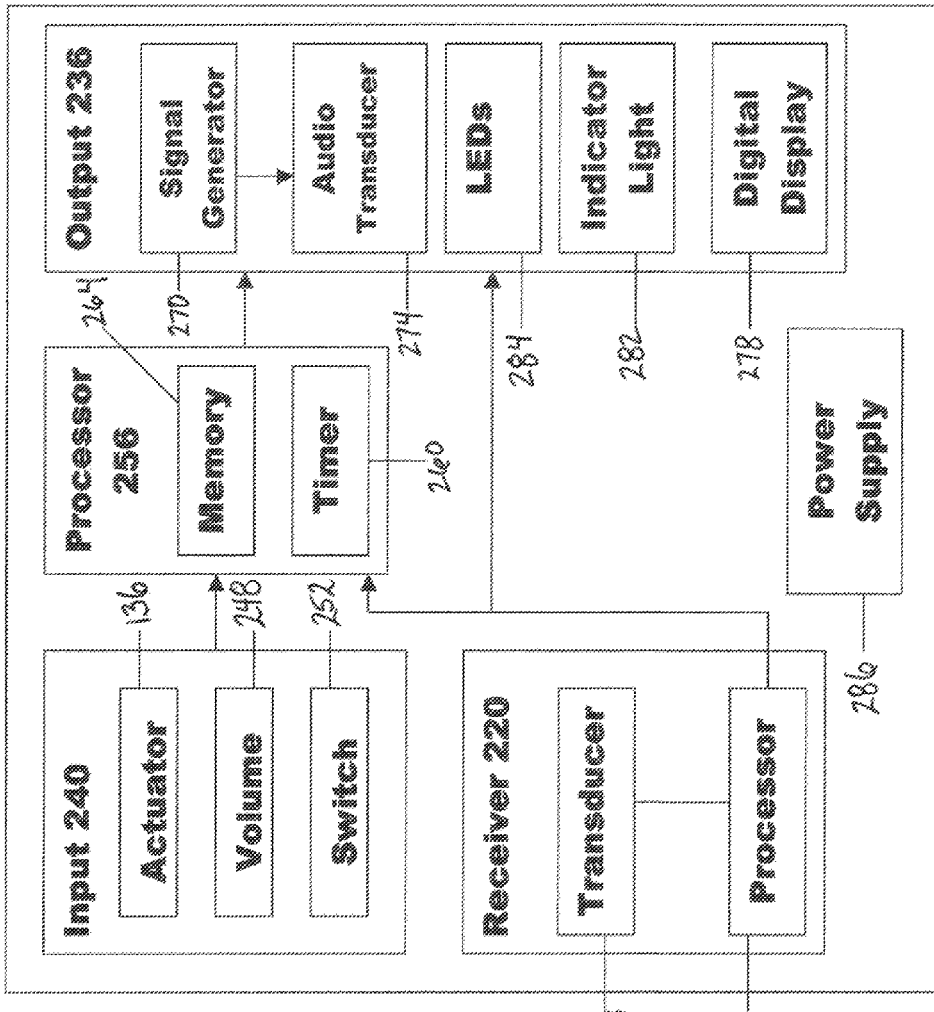
FIG. 2 is a functional block diagram of a baby monitor system in accordance with embodiments of the present invention.
Figure 2:
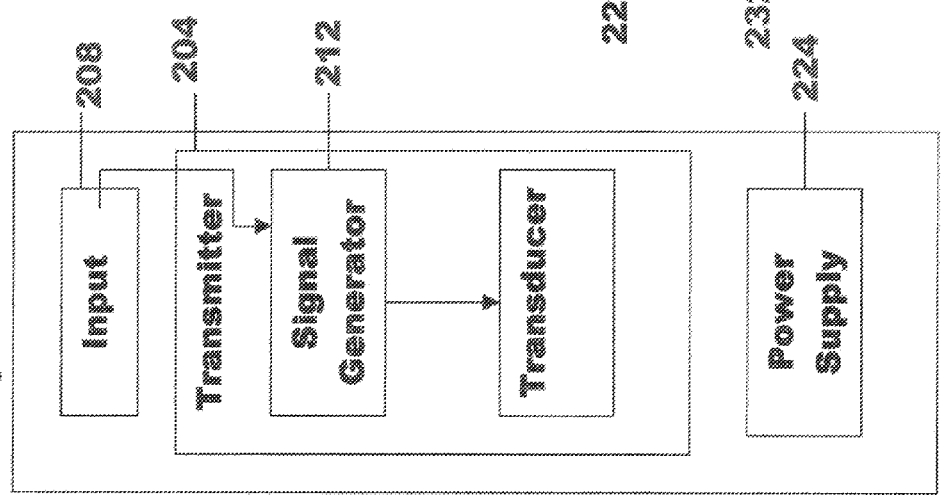

FIG. 2 is a functional block diagram of a baby monitor system 100 in accordance with embodiments of the present invention. The system includes a baby unit 118 and parent unit 132 in electronic communication through communication link 200. Preferably, the communication link 200 is a radio frequency communication link. Other types of communication links between the baby unit 118 and the parent unit 132 are within the scope of the invention. For example, the baby unit 118 and the parent unit 132 may communicate over a direct wired connection. Alternatively, the baby unit 118 and parent unit 132 may communicate over a local area network (LAN) used to interconnect electronic devices in the family home.

The baby unit 118 includes a transmitter portion 204 that receives input 208. The input 208 comprises audible sounds in the environment of the baby unit 118. Such audible sounds include cries or other sounds made by the baby 104. The transmitter portion includes a signal generator 212 and a transducer 216. The signal generator 212 operates to produce an electronic signal representative of the input 208. The transducer 216 operates to transmit the electronic signal over communication link 200 to a receiver portion 220 of the parent unit 132. In accordance with embodiments of the present invention, the transmitter portion 204 employs known radio frequency techniques such as frequency modulation, amplitude modulation or pulse width modulation. Additionally, the baby unit 118 includes a power supply 224. Preferably, the power supply 224 comprises a battery. Alternatively, the power supply 224 may comprise an AC power line.

The receiver portion 220 incorporated in the parent unit 132 includes a transducer 228 and a processor 232. The transducer 228 receives the electronic signal transmitted by the baby unit 118 over the communication link 200. The processor 232 processes the received signal in preparation to be sent to an output portion 236, also incorporated in the parent unit 132. In accordance with embodiments of the present invention, the receiver portion 220 uses appropriate known radio frequency techniques to demodulate the signal received over the communication link 200.

In addition to a receiver portion 220 and an output portion 236, the parent unit 132 also includes a user input portion 240. The user input portion 240 includes an actuator 136 operable to control timing and/or muting features of the present invention. In accordance with embodiments of the present invention, the output portion 236 also includes an audio volume control 248 and a toggle switch 252 operable to switch the parent unit 132 between different modes of operation. The actuator 136 and the toggle switch 252 are discussed in greater detail below.

The parent unit 132 additionally includes a processor unit 256 operable to receive user inputs 240 and to control the operation of the output portion 236. The processor 256 may be a hardwired control unit or a processor capable of executing program instructions. Accordingly, the processor unit 256 may include any general-purpose programmable processor, digital signal processor (DSP) or controller for executing application programming. Alternatively, the processor 256 may comprise a specially configured application specific integrated circuit (ASIC). Additionally, the processor 256 may included a timer 260 for use in connection with the temporary mute functionality, as described below.

The processor unit 256 may additionally include memory 264 for use in connection with the execution of the programming by the processor 256. The memory 264 may comprise solid-state memory resident, removable or remote in nature, such as DRAM and SDRAM. Where the processor 256 comprises a controller, the memory 264 may be integral to the processor 256. Additionally, the memory 264 may contain a digital representation of audio content used in connection with embodiments of the present invention described below.

The output portion 236 provides audio and visual output for the parent unit 132 based on signals received from the receiver portion 220 and the processor unit 256. The output portion 236 includes an audio signal generator 270 that converts the received audio signal to signals suitable to drive the audio transducer 274. Generally, the transmitter 204, receiver 220 and output 236 pathway uses know electronic communication techniques to substantially reproduce the input 208 received at the baby unit 118 at the parent unit 132. As such electronic methods inherently contain certain imperfections and the input 208 may not be perfectly reproduced, the baby sounds are herein described as being "substantially reproduced." In accordance with embodiments of the present invention, the output portion 236 additionally includes a digital display 278 of time information, an indicator light 282, and/or a visual display 284 of received sound levels for use in connection with embodiment of the present invention described below.

Additionally, the parent unit 132 includes a power supply 286. Preferably, the power supply 286 comprises a battery. Alternatively, the power supply 286 may comprise an AC power line.

Figure 3:
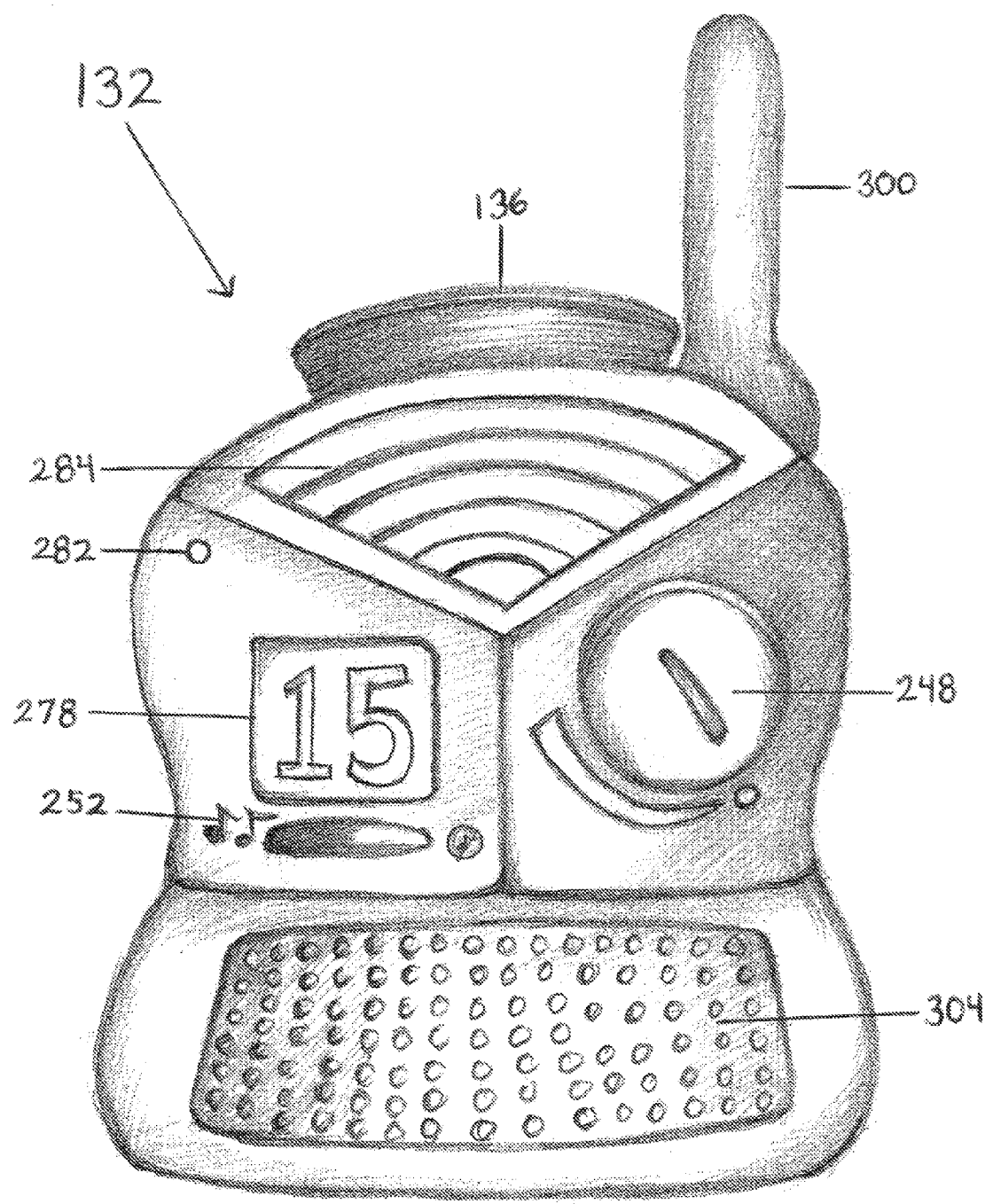
FIG. 3 is a front view of a parent unit of a baby monitor system in accordance with embodiments of the present invention.

FIG. 3 shows a detailed illustration of a parent unit 132 in accordance with embodiments of the present invention. The parent unit 132 includes an antenna 300 for receiving transmissions from the baby unit 118 and a speaker 304 for reproducing sounds made by the baby 104 that have been received from the baby unit 118. In accordance with embodiments of the present invention, the antenna 300 may comprise of a component of the communication link 200. Additionally, the speaker 304 may comprise a component of the audio transducer 274. The parent unit 132 may also include a volume control mechanism 248 that allows the volume of the substantially reproduced baby sounds to be adjusted.

The parent unit 132 includes functionality that allows the substantially reproduced baby sounds to be temporarily muted. In accordance with embodiment of the present invention, depressing actuator button 136, shown in FIG. 3 as being disposed on the top of the parent unit 132, enables this functionality. The baby's parents 126 or caregivers may utilize this functionality at a time when they wish to let the baby 104 cry for a certain time without receiving attention. Enabling the temporary muting functionality silences the parent unit's 132 reproduction of sounds made by the baby 104 for a predetermined time. After the predetermined time has elapsed, the temporary muting functionality is disabled and the parent unit 132 again substantially reproduces sounds made by the baby 104.

Parent unit 132 may remain muted for a fixed amount of time. Alternatively, the present invention may include functionality that allows for the amount of time that the parent unit 132 remains muted to be adjusted. In accordance with embodiments of the present invention, the time that the parent unit 132 remains muted is kept by the timer 260 and may be adjusted by repeatedly depressing actuator button 136. In particular, a depression of the actuator button 136 results in an increment of time being added to the time remaining before the temporary muting functionality is disabled. Time may be added to the timer 260 in a series of increments such as 2, 5, 10, 15, 20, 30 60 and 90 minutes. Accordingly, one depression of the actuator button 136 results in a muting time of two minutes, two depressions result in a muting time of five minutes, and so on. Other series of time increments are within the scope of the invention. For example, time may be added in series of increments such as 1, 2, 3, 4, 5, et cetera. Additionally, the series of time increments may repeat after a certain amount of depressions of the actuator button 136. For example, referring to first example above, nine depressions of the actuator button 136 would result in a time interval of two minutes. In accordance with embodiments of the present invention, parent unit 132 includes a digital display 278 that shows the time (kept by timer 260) remaining before the temporary muting functionality is disabled.

In accordance with embodiments of the present invention, the parent unit 132 includes a mode in which an alternative audio content is played when the temporary muting functionality is enabled. For example, the parent 126 or caregiver enables the temporary muting functionality and the parent unit 132 plays classical music instead of sounds made by the baby 104. Alternatively, other music genres are within the scope of the invention. The toggle switch 252, described above in connection with user input portion 240, turns this mode on and off FIG. 3 shows the toggle switch 252 disposed on the face of the parent unit 132.

In accordance with embodiments of the present invention, the parent unit 132 may include a visual display 284 indicating the presence and/or volume of sounds currently being made by the baby 104. As can be appreciated by one of skill in the art, such a visual display 284 may consist of a series of light emitting diodes or other electronic indicators appropriately arranged to indicate sound level.

In accordance with embodiments of the present invention, the parent unit 132 may include an indicator light 282 illuminated at such times when the temporary muting functionality is enabled. FIG. 3 shows this indicator light 282 disposed on the face of the parent unit 132.

It may be desirable for the baby monitor system 100 to include one or more safety features that operate to disable the temporary muting functionality in response to sounds made by the baby 104. For example, if the sounds made by the baby 104 exceed a certain volume this may indicate an emergency situation requiring attention by the parents 126 or caregivers. Accordingly, embodiments of the present invention provide a parent unit 132 that measures the volume of the sounds made by the baby 104 and compares the measurement with a predetermined threshold. If the measured volume exceeds the predetermined threshold, the temporary muting functionality is disabled and, immediately, the parent unit 132 substantially reproduces sounds made the baby 104. The processor 256 may carry out such measurement and comparison calculation. Alternative safety features are also within the scope of the invention. In particular, pattern recognition techniques may be used to identify baby cries that are indicative of particular needs.

Figure 4:
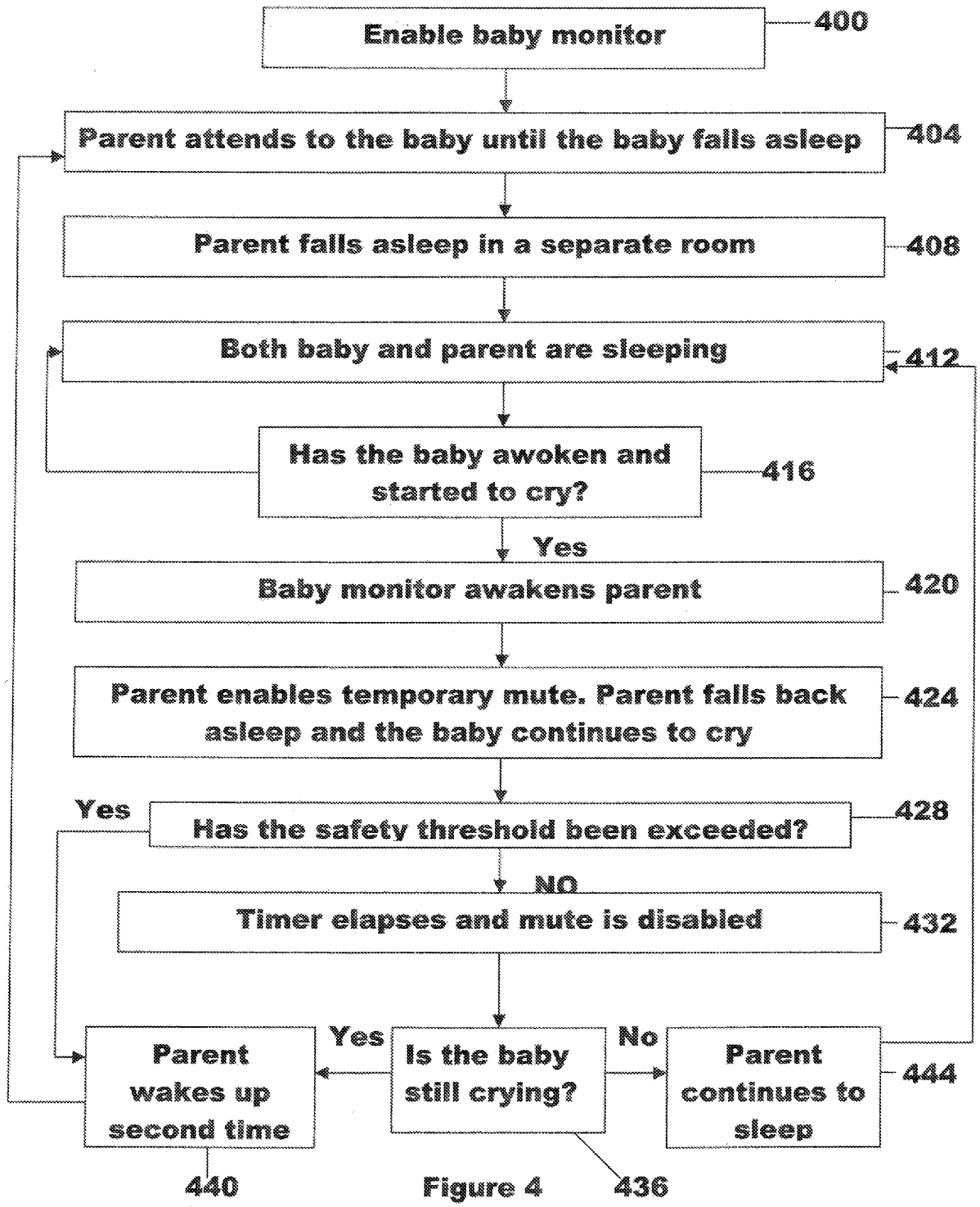
FIG. 4 is a block diagram of a method of monitoring a baby in accordance with embodiments of the present invention.

Turning now to FIG. 4, a method of monitoring a baby in accordance with embodiments of the present invention is shown in block diagram form. At step 400, the baby monitor system 100 is enabled. In particular, baby unit 118 and parent unit 132 are turned on and placed in appropriate locations. The baby unit 118 is placed sufficiently close the baby's bed or crib 108 to allow crying or other noises made by the baby to be picked up. The parent unit 132 is placed in a location convenient for the parents 126 at such times when the baby 104 needs to be monitored.

At step 404, the parent 126 or caregiver puts the baby 104 down for sleep. Additionally, at step 404, the parent attends to the baby's 104 needs in an attempt to soothe the baby 104 to sleep. Examples of such soothing gestures known to parents include singing lullabies and reading stories. At such time that the parent 126 decides the baby 104 should be left alone, he or she retires to a different room in the family home. Preferably, the parent 126 retires after the baby 104 has gone to sleep, but as can be appreciated this is not always the case.

At step 408, the parents 126 or caregivers lie down for sleep. In accordance with embodiments of the present invention, enabling the parent unit 132 may occur at step 408 when the parents 126 are lying down for sleep as opposed to initially at step 400. At step 412, both the baby 104 and the parents 126 remain sleeping. Alternatively, embodiments of the present invention include methods wherein the baby monitor system 100 is used at times when the parents 126 are not sleeping. For example, the baby monitor system 100 may be used when the parents 126 are preparing a meal in the kitchen. The parents 126 may use the baby monitor 100 at any time when they are located in a room of the house that is removed from the nursery 114 and desire to monitor the baby 104.

At step 412, the baby monitor 100 remains in operation, and if the baby 104 continues to sleep the parents are not woken-up. Accordingly, the baby 104 and the parents 126 continue to sleep. However, if at step 416, the baby 104 awakens and begins to cry, step 420 follows.

At step 420, operation of the baby monitor system 100 causes the parents 126 to awaken. In particular, the baby's 104 cries are picked-up by the baby unit 118 and transmitted to the parent unit 132. At the parent unit 132, the baby's 104 cries are substantially reproduced at sufficient volume to awaken the parents 126.

At step 424, the parents 126 determine that they will let the baby 104 cry for a amount of time. As discussed above, the decision to let the baby 104 cry is made in an attempt to foster independence and greater maturity in the baby 104. Additionally, it is hoped that the baby 104 will cry itself back to sleep. Accordingly, the parents 126 enable parent unit's 132 temporary muting function. As described above this may be accomplished by depressing actuator button 136. In accordance with embodiments of the present invention, step 420 may include setting a time (kept by timer 260) in which the temporary muting function remains enabled. This may be accomplished by repeated actuations of the actuator 136. When the parents 126 determine that sufficient time has been added, they fall back asleep.

At step 424, the parent unit 132 remains muted, the parents 126 continue to sleep, and the baby 104 continues to cry. Baby monitoring methods in accordance with embodiments of the present invention may include safety features operable to disable the temporary mute function in the event that a possible emergency situation is detected. For example, the mute function may be disabled when the volume of the cries or other sounds made by the baby 104 exceeds a certain threshold level. Accordingly, at decision 428, if the threshold level is exceeded the temporary mute function is disabled and the parents 126 wake-up a second time (step 440). If, however, the baby's 104 cries do not exceed the threshold level, the parent unit 132 remains muted until step 432.

At step 432, the timer 260 expires and the temporary mute function is disabled. As a result, the parent unit 132 is again allowed to substantially reproduce cries or other sounds made by the baby 104. Whether or not the baby 104 is still crying (decision diamond 436), will determine if the parents 126 wake-up a second time. If the baby 104 is still crying, the parents 126 will wake-up a second time (step 440) and then proceed to attend to the baby 104 (step 404). At this point the method will proceed as described above. Alternatively, if the baby 104 has fallen back asleep, the parent 126 will continue to sleep (step 440). Accordingly, both the baby 104 and the parents 126 are sleeping (step 412) and the method proceeds as described above. The method of monitoring a baby in accordance with present invention continues in this manner throughout the night until such time that the parents 126 wake-up the next morning to begin the next day.

The following U.S. Patents are incorporated by reference in their entirety: U.S. Pat. Nos. 7,049,968; 6,150,941; and 6,043,747.

The present invention, in various embodiments, includes components, methods, processes, systems and/or apparatus substantially as depicted and described herein, including various embodiments, sub combinations, and subsets thereof. Those of skill in the art will understand how to make and use the present invention after understanding the present disclosure. The present invention, in various embodiments, includes providing devices and processes in the absence of items not depicted and/or described herein or in various embodiments hereof, including in the absence of such items as may have been used in previous devices or processes, e.g., for improving performance, achieving ease and\or reducing cost of implementation.

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the invention.

Moreover though the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A baby monitor system, comprising:
    a baby unit configured to detect an audible sound and configured to transmit a signal representative of the detected audible sound via a communication link;
    a parent unit configured to receive, via the communication link, the signal transmitted by the baby unit and configured to substantially reproduce the audible sound based on the received signal;
    an actuator configured to activate a temporary muting function of the system for a determined period of time, the temporary muting function temporarily disabling the reproduction of the audible sound by the parent unit during the determined period of time; and
    a mode selector configured to place the system in one of at least two modes of operation including a silence mode in which the temporary muting function operates to cause the parent unit to output no sound during the determined period of time and a music mode in which the temporary muting function operates to cause the parent unit to output music during the determined period of time.

2. The baby monitor system of claim 1, wherein the actuator comprises a button disposed on the parent unit.

3. The baby monitor system of claim 1, further comprising:
a timer configured to time elapse of the determined period of time, wherein after an elapse of the determined time timed by the timer the temporary muting function is no longer activated; and
wherein actuating the actuator activates the temporary muting function and sets the timer to the predetermined time.

4. The baby monitor system of claim 3, wherein the determined period of time is one of a series of predetermined increases of time, wherein iterations of actuating the actuator cause sequential selection of the series of predetermined increases of time for the determined period of time.

5. The baby monitor system of claim 4, wherein the series of predetermined increases of time includes a maximum at an end of the series; and wherein an iteration of actuating the actuator after an iteration of the actuator that selects the maximum restarts the sequential selection of the series of predetermined increases of time at a start of the series.

6. The baby monitor system of claim 1, wherein the temporary muting function temporarily disabling the reproduction of the audible sound by the parent unit during the determined period of time comprises disabling at least one of detection of the audible sound by the baby unit, transmitting of the signal by the baby unit, and receiving of the signal by the parent unit.

7. The baby monitor system of claim 1, wherein the communication link comprises a radio frequency communication link.

8. The baby monitor system of claim 1, wherein the communication link comprises a local area network.

9. A method of monitoring using a baby monitoring system, comprising:
detecting an audible sound at a baby unit of the baby monitoring system;
transmitting a signal representative of the detected audible sound;
receiving the transmitted signal at a parent unit of the baby monitoring system;
based on the transmitted signal, substantially reproducing the audible sound at the parent unit when
a temporary muting function of the baby monitoring system is not activated;
outputting no sound at the parent unit when the temporary muting function is activated and the baby monitoring system is in a first mode of operation; and
outputting music at the parent unit when the temporary muting function is activated and the baby monitoring system is in a second mode of operation.

10. The method of claim 9 further comprising:
enabling a timer when the temporary muting function is activated, wherein an elapsing of the timer causes the temporary muting function to be deactivated; and
displaying a time remaining before the elapsing of the timer.

11. The method of claim 10, further comprising activating the temporary muting function in response to a user input received by the baby monitoring system.

12. The method of claim 11, wherein activating the temporary muting function activates the function for a determined period of time based on the received user input.

13. The method of claim 12, wherein the determined period of time is one of a series of predetermined increases of time sequentially selected by iterations of the received user input.

14. The method of claim 13, wherein the series of predetermined increases of time includes a maximum at an end of the series and an iteration of the received user input received after an iteration of the received user input that selects the maximum restarts the sequential selection of the series of predetermined increases of time at a start of the series.

15. The method of claim 9, further comprising determining one of the first mode of operation and the second mode of operation for the baby monitoring system.

16. The method of claim 15, wherein the determining comprises determining a status of a switch of the baby monitoring system.

17. The method of claim 15, wherein the determining comprises determining a user selection of one of the modes of operation.

18. A baby monitor system, comprising:
means for detecting an audible sound;
means for transmitting a signal representative of the detected audible sound;
means for receiving the transmitted signal remote from the means for detecting and the means for transmitting;
means for substantially reproducing the audible sound based on the received signal;
means for activating a temporary function of the system for a determined period of time, the temporary muting function temporarily disabling, during the determined period of time, reproduction of the audible sound by the means for substantially reproducing; and
means for selecting a mode of operation of the system to place the system in one of at least two modes including a silence mode in which the temporary muting function operates to cause no sound to be output remote from the means for detecting and the means for transmitting during the determined period of time and a music mode in which the temporary muting function operates to cause music to be output remote from the means for detecting and the means for transmitting during the determined period of time.

19. The baby monitor system of claim 18 further comprising: means for timing a time interval that the temporary muting function remains activated, wherein after an expiration of the time interval the temporary muting function is no longer activated.

20. The baby monitor system of claim 18, further comprising: means for providing output from the means for substantially reproducing when the temporary muting function is not activated and output of music when the system is in the music mode and the temporary muting function is activated.

\* \* \* \* \*